United States Patent [19]

De Pous et al.

[11] Patent Number: 5,484,515

[45] Date of Patent: * Jan. 16, 1996

[54] DEVICE FOR GENERATING AN ELECTRIC SIGNAL LINEARLY DEPENDENT UPON THE OXYGEN CONTENT OF A GASEOUS MIXTURE

[75] Inventors: Olivier De Pous, Geneva, Switzerland; Gérard Horlaville, La Roche sur Foron, France

[73] Assignee: Honda Motor Company Ltd., Tokyo, Japan

[ * ] Notice: The portion of the term of this patent subsequent to Aug. 7, 2007, has been disclaimed.

[21] Appl. No.: 256,193

[22] Filed: Oct. 11, 1988

Related U.S. Application Data

[63] Continuation of Ser. No. 17,009, Feb. 19, 1987, abandoned, which is a continuation of Ser. No. 706,864, Feb. 28, 1985, abandoned.

[30] Foreign Application Priority Data

Mar. 5, 1984 [EP] European Pat. Off. ............. 84810105

[51] Int. Cl.$^6$ .................................................. G01N 27/407
[52] U.S. Cl. ...................... 204/425; 204/153.18; 204/427
[58] Field of Search ................................ 204/15, 421–429

[56] References Cited

U.S. PATENT DOCUMENTS

| | | | |
|---|---|---|---|
| 3,400,054 | 9/1968 | Ruka et al. | 204/153.18 |
| 3,691,023 | 9/1972 | Ruka et al. | 204/425 |
| 3,843,489 | 10/1974 | Sandler | 204/425 |
| 3,883,408 | 5/1975 | Kim et al. | 204/424 |
| 3,989,614 | 11/1976 | Tien | 204/427 |
| 4,119,512 | 10/1978 | Inoue et al. | 204/429 |
| 4,121,988 | 10/1978 | Sano et al. | 204/429 |
| 4,145,272 | 3/1979 | Nakamura et al. | 204/428 |
| 4,151,060 | 4/1979 | Isenberg | 204/428 |
| 4,158,166 | 6/1979 | Isenberg | 204/153.8 |
| 4,172,247 | 10/1979 | Ikeura | 204/424 |
| 4,189,355 | 2/1980 | Fujishiro et al. | 204/153.18 |
| 4,199,424 | 4/1980 | Teitelbaum | 204/428 |
| 4,230,555 | 10/1980 | Sano et al. | 204/427 |
| 4,394,222 | 7/1983 | Rohr | 204/153.18 |
| 4,402,820 | 9/1983 | Sano et al. | 204/425 |
| 4,407,704 | 10/1983 | Mase et al. | 204/425 |
| 4,502,939 | 3/1985 | Holfelder et al. | 204/429 |

*Primary Examiner*—T. Tung
*Attorney, Agent, or Firm*—Cushman Darby & Cushman

[57] ABSTRACT

This sensor, which is of the oxygen pump type, makes it possible to generate an electric signal representative of the oxygen content of a gas, linearly dependent on this oxygen content, made of a solid electrolyte plate (3), one of whose faces is partly covered by a cathode (1) impervious to oxygen to be brought into the presence of the said gas, and whose other face is covered by an anode (2) to be brought into the presence of a reference gas. Under the effect of the difference in potential prevailing between the two electrodes (1, 2), there appears at the surface of the solid electrolyte an area (I) in which the molecular oxygen contained in the said gas is transformed into negative ions. The electrons captured by the oxygen during this transformation produce the said electric signal.

9 Claims, 4 Drawing Sheets

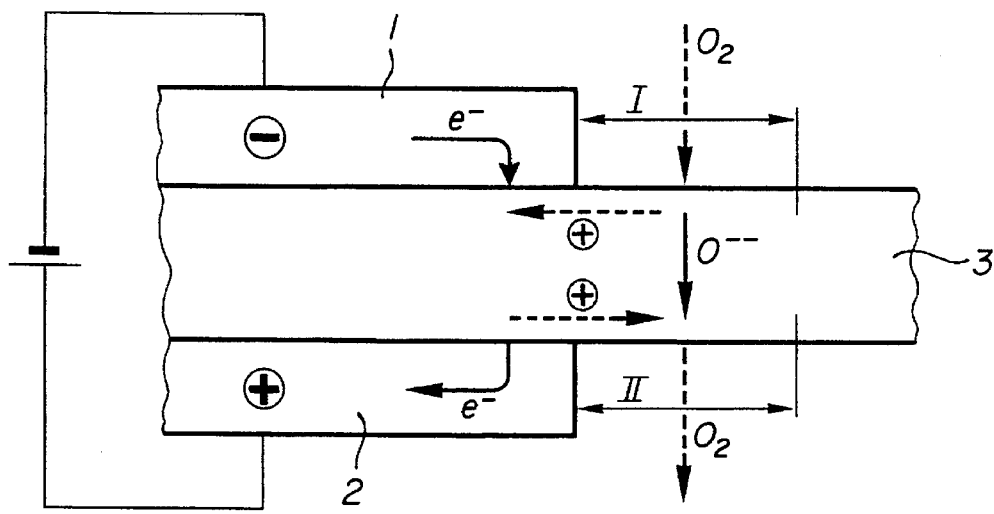
FIG. 1
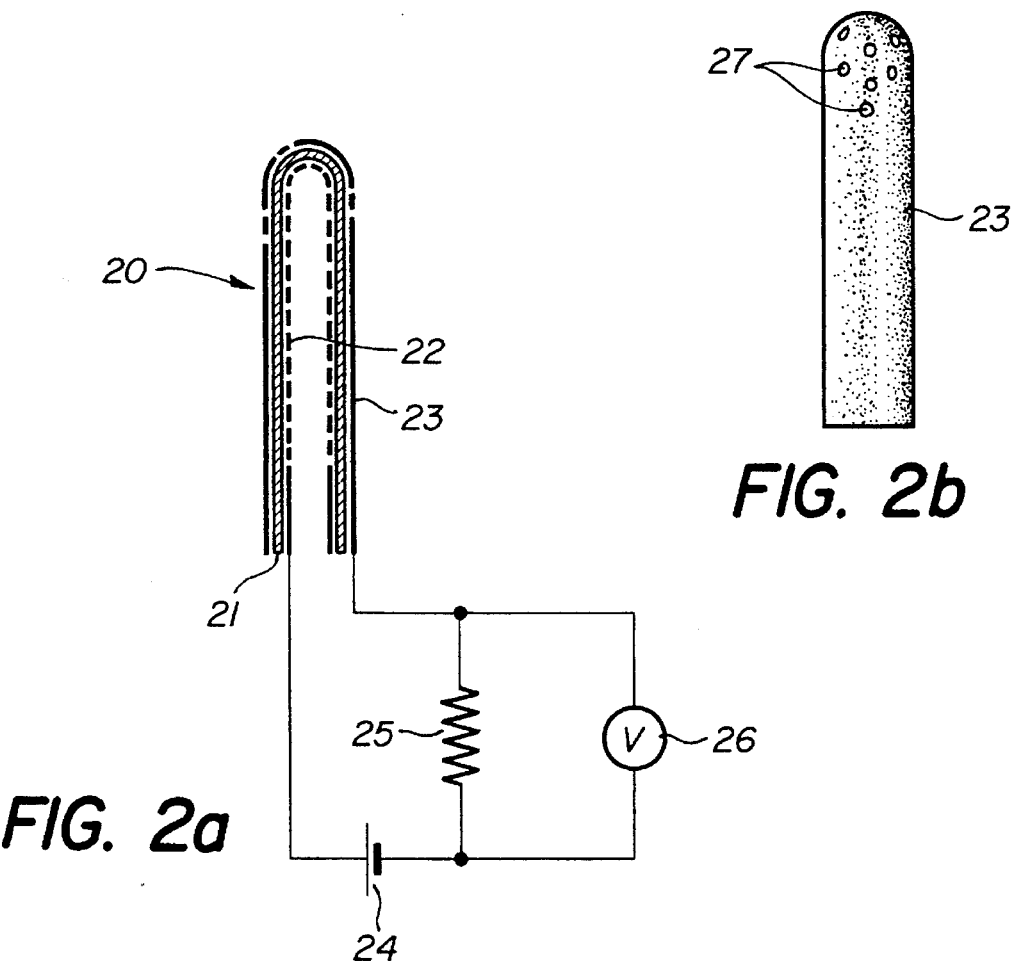
FIG. 2b
FIG. 2a

DEVICE FOR GENERATING AN ELECTRIC SIGNAL LINEARLY DEPENDENT UPON THE OXYGEN CONTENT OF A GASEOUS MIXTURE

This is a continuation of application Ser. No. 07/017,009, filed Feb. 19, 1987, now abandoned, which was a continuation application of Ser. No. 06/706,864, filed Feb. 28, 1985, now abandoned.

The object of the present invention is to provide a method and device for generating an electric signal characteristic of the oxygen content of a gaseous mixture and suitable for determining this content.

Amongst the known solutions for measuring the quantity of oxygen contained in a gaseous mixture, devices exist which are formed by a solid electrolyte membrane on each side of which a porous electrode is fixed. This membrane separates the gaseous mixture to be analysed from a reference gas. If the oxygen content of this mixture is different from that of the reference gas, an electric potential is generated which is a logarithmic function of the oxygen concentrations difference in the two gases. Measuring this potential and knowing the oxygen content of the reference gas makes it possible to determine the oxygen content of the gaseous mixture.

A method of manufacturing porous electrodes used for this type of sensor is disclosed in U.S. Pat. No. 4 372 824. In this method an electrode is placed on a solid electrolyte and is then subjected to a heat treatment capable of increasing its porosity. The aim of this treatment is to favour the penetration of the oxygen into the solid electrolyte so as to improve the sensitivity of the sensor.

The logarithmic behaviour of these sensors makes them very efficient for measuring small oxygen concentrations (less than 0,5%). They are, however, not well adapted for determining higher concentrations of oxygen and furthermore, the response of such sensors remains largely dependent on temperature.

In order to remove these disadvantages, sensors of the oxygen pump type have been proposed. These sensors are formed, as mentioned above, by a solid electrolyte membrane the opposite sides of which are covered with a porous electrode. The originality of this type of sensor lies in the fact that the electrodes are connected to a source of electric power which promotes the formation of oxygen ions o⁻ at the cathode and causes the migration thereof across the membrane and in the fact that this cathode is coated with an element designed to limit the flow of oxygen-containing gas capable of migrating across this membrane.

This element may be formed by a porous ceramic layer integral with said cathode such as disclosed in patent application published before examination, JP 57-48648, where the porosity of the ceramic layer was chosen such that, in normal conditions of use of the sensor, this layer limits in a well-defined manner the flow of gas capable of coming into contact with the cathode. Therefore, the flow of molecular oxygen to be transformed into ions which migrate through the solid electrolyte is proportional to the difference in the oxygen partial pressures which exist on both sides of the membrane. The value of the electric current flowing across the electrodes which result from the migration of the oxygen ions across the solid electrolyte membrane is, therefore, a characteristic of the oxygen content of the gas passing into the ceramic layer.

Furthermore, an element for limiting the oxygen flow having the form of a capsule comprising a calibrated orifice is known from patent application JP 52-72286 published before examination.

In order to obtain good performance from this type of sensor, there is advantage in having electrodes whose porosity is very high so as to favour as much as possible the penetration of the oxygen into the solid electrolyte.

Sensors of the oxygen pump type using this type of limitation of the flow of oxygen-containing gas have various major drawbacks. The solid particles possibly suspended in the gaseous mixture to be analyzed tend to plug the pores of the ceramic layer or to alter the cross-section of the capillary pores, which will restrict the flow of oxygen through the sensor so that the behaviour thereof may change with time. Moreover, the response time of such sensors is generally very long and therefore they are not well-suited when it is necessary to measure rapid variations in the oxygen content of a gas. This excessive response time is mainly due to the dynamic characteristics of the gaseous flow in the element which limits the flow of oxygen-containing gas through the probe.

Patent CH 478 463 discloses an electrode which can be used in a solid electrolyte fuel cell. This electrode is formed by an underlayer consisting of a fritted electron and ion conductive ceramic material, which is applied to a solid electrolyte substrate such as zirconia and by a porous layer having good electronic conductivity and integral with said underlayer. This electrode is designed to allow a large quantity of oxygen to pass into the solid electrolyte.

The state of the art also comprises DE-A-1.954.663 which discloses an oxygen measuring probe comprising an anode and a cathode whose surface is largely in electrical contact with a solid electrolyte body in a manner such that one electrode can be brought into contact with a reference gas containing oxygen while the other electrode can be contacted with an oxygen containing gas to be analyzed; and the electrodes are connected to a voltage source via an ammeter for measuring the current flowing between the electrodes and the electrolyte body. The electrodes are porous and would not be operative unless this is so.

DE-A-2.906.459 discloses a probe for measuring oxygen in gases which also comports a solid electrolyte conductive of $O^-$ ions and, in electrical contact therewith, two electrodes, a measuring electrode and a reference electrode contacted by oxygen at a (partial) pressure of reference. This oxygen at a reference partial gaseous pressure is provided by dynamic means, i.e. by controlling the amount of an oxygen containing gas (air) coming into contact with, or leaving the reference electrode, by passing it through a porous structure that physically isolates the reference electrode from the outside. This porous structure can consist of either the electrode itself (which can be made porous to gases in molecular form) or by a shield applied over the reference electrode (see the drawing, FIGS. 1 to 5).

DE-A-3.313.783 discloses an apparatus for measuring the concentration of oxygen in a gas, namely in the exhaust gases of an internal combustion engine. One element of this apparatus is a detecting probe illustrated on FIG. 1 and described at pages 10–12. This probe consists essentially of a layer of solid electrolyte and two electrodes 4 and 5, one of them (4) in contact with the exhaust gases and the other (5) with the atmosphere (reference) through a porous sheet 3. Both the electrodes have a porous structure.

Document FR-A-2.358.655 discloses a device for measuring oxygen in gases including free oxygen (molecular oxygen) and bound oxygen, i.e. oxygen as a moiety in gaseous compounds such as $CO_2$, CO, $NO_2$, etc. One embodiment of such device is illustrated at FIG. 1 and described at pages 7 and 8. It comprises a solid electrolyte 12 conductive of $O^-$ ions, a measuring electrode 13 and a counter-electrode 14. When a voltage sufficient to ensure the circulation of oxygen ions through the electrolyte is applied to the electrodes and in the presence of an oxygen containing gas around electrode 13, a current proportional to the oxygen content of the gas under test will circulate. The electrode may be porous but not necessarily so (see pages 5, line 21). Further, according to the drawing, there exists like in the aforediscussed embodiment of DE-A-2.906.459 areas of the electrolyte uncovered by the test electrode but still in contact with the gas under test. This implies the existence of boundary lines at the junction of the electrode with the electrolyte, the latter extending freely on both sides of the electrode and allowing the formation of an $O^-$ ion current flow.

Document US-A-4,373,824 discloses the manufacture of oxygen sensors composed of a solid electrolyte structure coated on each side with an electrode permeable to oxygen containing gases.

At least one of these electrodes (see the Example, col. 6) consists of a platinum layer about 1 μm thick with holes about 5–6 μm average diameter therein for allowing the test gas to get across the electrode and come into contact with the electrolyte.

Thus, in nearly all the embodiments of the prior art when an electric current is generated by a flow of oxygen ions migrating through a solid electrolyte, this electrolyte is coated with at least two high porosity electrodes. No embodiment appears to exist yet in which a dry electrolytic probe cell is used with a solid electrolyte and electrodes in contact therewith of which at least the cathode is non porous and in which the conductive parameters of the electrolyte in the area very close to the boundary line between the cathode and said electrolyte are distinctive for the determination of the oxygen in a gas brought into contact with said area.

In order to remedy the shortcomings in the existing sensors, and improve their performance, the present invention relates first to a method for measuring oxygen in a gas with particular reference to a sensor with a very simple structure enabling an electric signal characteristic of the oxygen content of a gaseous mixture and linearly dependent on this oxygen content to be generated. This signal may even be independent of the temperature of the sensor if the characteristics of the sensor and the parameters of use are suitably chosen.

This may be done where the ratio of the ionic resistance of the electrolyte to the length of the cathode-electrolyte boundary is less than $10^4$ ohm/cm, and where the ratio of the voltage applied to the electrodes to the length of the cathode-electrolyte boundary ranges from 0.2 to 20 volts/cm. This sensor device can be designed for measuring the oxygen content of the exhaust gases of an internal combustion engine.

The attached drawings illustrate schematically and by way of example the structure and the operation of an embodiment and a variant of the sensor cell according to the invention. In the drawings:

FIG. 1 is a section thereof in simplified form,

FIG. 2a is a schematized representation of a variant and its use according to the invention, FIG. 2b is a perspective schematized view of an electrode suitable for the device of the invention.

Figure 3:
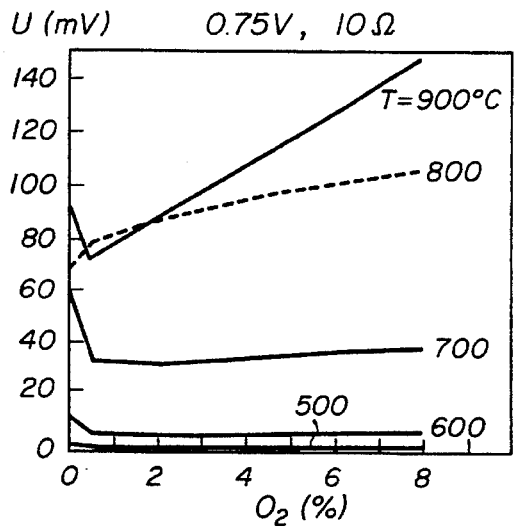
FIGS. 3 to 14 are graphs illustrating the behaviour of other variants of the sensor according to the invention.

The device of FIG. 1 comprises a negatively polarised electrode 1 (cathode) and a positively polarised electrode 2 (anode) both of which, connected to a DC source, are impervious to oxygen gas. The sensor may be between 10 and 1000 μm thick. Each electrode is fixed on one of the faces of an oxygen ion-conductive solid electrolyte body or substrate 3, each of these faces being brought into contact with an oxygen-containing gas. The cathode 1 is contacted with the gas under test and anode 2 is contacted with a reference gas containing a known amount of oxygen. When an electric D.C. potential is applied to the electrodes, negative charges (electrons) accumulate in the cathode 1 and in an area I of the surface of the electrolyte adjacent the said electrode 1 negative oxygen ions are formed by ionization of the gas ($O_2 \leftrightarrows 2\ O^-$). The $O^-$ ions migrate towards the anode where they are neutralised by losing their negative charge therein and reforming oxygen gas molecules which are then returned to the surrounding environment from an area II of the electrolyte body. This ion flow, therefore, generates in the cell across the electrodes 1 and 2 an electric current proportional to the number of ionized molecules flowing through the electrolyte.

The quantity of ionized oxygen formed per unit of time is linearly dependent on the extent of area I, on the magnitude of the potential applied to the electrodes, on the number of oxygen molecules in contact with areas I and II, i.e. the oxygen concentrations (partial pressures) of the gaseous media in contact on both sides of the electrolyte.

In addition it must be added that for a given oxygen content of the gaseous medium and a specified extent of the area I, the number of oxygen molecules capable of coming into contact with the area I is inversely proportional to the square root of the temperature of the gaseous medium.

The size of the area II may influence the maximum quantity of oxygen returned to the gaseous medium if its extent is less than that of the area I. Therefore the area II will be the same or larger than area I.

Moreover, the ionic resistance per unit of surface of a solid electrolyte diminishes exponentially with the temperature and is inversely proportional to the distance of migration of the ions into the electrolyte.

Experience has shown that a device functioning according to the above principle can generate a signal linearly representative of the oxygen content of a gaseous mixture and that the dependence of this signal with respect to temperature can even be virtually cancelled. To this end, it is sufficient to choose the arrangement and the geometry of the electrodes, the thickness of the solid electrolyte and the value of the potential difference applied between these electrodes in such a way that the area I has a dominating influence on the quantity of ionized oxygen per unit of time. This is particularly so with a geometry such that when the flow of ionised oxygen into area I is significantly less than the maximum ion flow which could possibly be caused to migrate into the electrolyte. This ion flow is dependent on the resistance of the electrolyte, therefore on the temperature and the potential difference applied between the electrodes by the source 5.

Moreover, the anode 2 does not necessarily have a structure similar to the cathode 1. For example, for this electrode 2 any known prior art porous electrode can be used so that the ion flow is only limited by the geometry of the cathode 1.

Those skilled in art will note that this device can also be used to measure the amount of oxygen contained in a gaseous mixture whose temperature is lower than 500° C. As a matter of fact, it is sufficient in such a case to complete said sensor by adding means for heating, for example an electric resistance, to carry and/or maintain this sensor at a temperature of at least 500° C.

FIG. 2 shows an installation including a sensor 20 according to the invention, formed by a solid electrolyte tube 21 closed at its top end and covered on its inner surface by a conventional porous anode 22, and on its outer surface by an cathode 23, which is impervious to oxygen, partly covering this outer face. The anode 22 is connected to the positive terminal of an electric source of 24, whereas the cathode 23 is connected to the negative terminal of the same source. A voltmeter 26, connected in parallel to the terminals of a resistor 25, itself connected in series between the electrode 23 and the source 24, makes it possible to measure the electric current flowing into the electrodes 22 and 23.

An example of an electrode according to the invention is schematically represented on FIG. 2b, in which little holes 27 are distributed on a portion of the electrode surface 23; these holes in the cathode 23 enable the gas to be measured to come into contact with the electrolyte 21 on the underside of the cathode.

The graphs in FIGS. 3 to 14 illustrate the behaviour of three sensors according to the invention described in the following examples. In FIGS. 3, 4, 5, 9 and 11 representing the behaviour of these sensors as a function of the oxygen content of a gaseous mixture, the voltage measured at the terminals of the resistor 25 is plotted on the ordinate axis whereas the oxygen content is plotted on the axis of abscissae. Each graph corresponds to a temperature value of the gaseous mixture. FIGS. 6 to 8, 10 and 12 to 14 show the response of the same sensors as a function of the temperature. The value of the voltage at the terminals of the resistor 25 was plotted on the ordinate axis and the temperature of the gaseous mixture on the axis of abscissae. Each graph shows the behaviour of the sensor for a given value of the oxygen content of the gaseous mixture.

The three sensors according to the invention, the results of which are summarized in FIGS. 3 to 14, were used in an installation according to FIG. 2a. Each sensor was formed by a tube 21 of zirconia stabilised by yttrium oxide at concentration of 7.5 moles %, closed at one of its ends and having a wall of average thickness of the order of 0.5±0.05 millimeters, an average diameter of 3.2 millimeters and 40 millimeters long.

Firstly, the value of the ionic resistance of such tubes was estimated. For this purpose, sensors whose electrodes were connected to a source of electric potential were placed in a medium rich in oxygen and the intensity of the electric current flowing across the electrodes for a given potential was measured. The value of the ionic resistance was calculated from this value of current and from the voltage applied by using Ohm's law. Thus resistances less than $10^4$ Ohm for measurements taken at more than 500° C. were obtained.

Example 1

An electrode with high porosity on the inner face of the zirconia tube was obtained by decomposition of a layer of ammonium chloroplatinate at a temperature of approximately 450° C.

An outer electrode, sufficiently thick to be impervious to oxygen and made of platinum was built up on the external portion of the tube. This was cylindrical in form and extended over a length of approximately 3.6 cm starting from the open end of the tube, thus providing an uncoated annular area of approximately 1 cm circumference in contact of which molecular oxygen could be transformed into negative ions. This electrode was obtained by cathode sputtering in an argon atmosphere at a pressure of 0.1 mm of Hg. The glow discharge current was 25 mA, and the constant voltage between the platinum target and the anode was 250 volt. The depositing process carried out for approximately 3 minutes and 30 seconds made it possible to obtain an electrode impervious to oxygen and approximately 1.2 μm thick. In the course of this depositing operation, a detachable mask covering the portion of the tube to stay uncoated was used.

Figure 4:
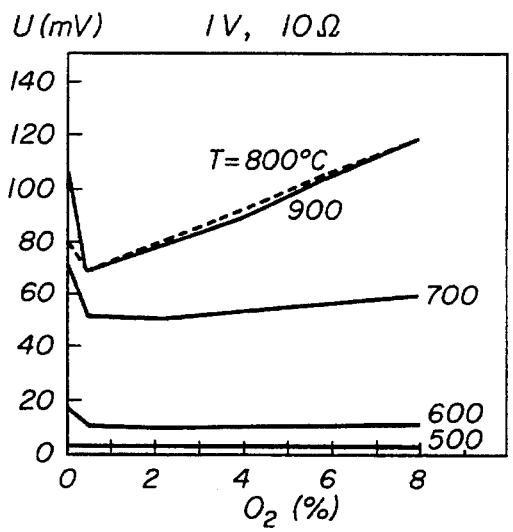

The behaviour of such a sensor incorporated in an installation according to FIG. 2a made it possible to draw up the graphs of FIGS. 3 to 9, the reference gas used being air brought into the presence of the anode 22 inside of the tube. FIGS. 3 and 4 show the development of the voltage at the terminals of a resistor 25 of a value of 10 Ohm placed in series with the electrode circuit. It is noted that this voltage, proportional to the value of the current flowing into the electrodes 22, 23, is linearly dependent on the oxygen content of the gaseous medium in the presence of the electrode 23 for measurements made at more than approximately 500° C., and for oxygen contents above approximately 0.4%. The voltage at the terminals of the source 24 was 0.75 volt in the case of the chart in FIG. 3, and 1 volt in the case of the chart in FIG. 4. The resistance of resistor 25 may be considered negligible with respect to the resistance of the sensor in the temperature interval at which the tests were carried out and the voltage between the electrodes 22 and 23 is consequently close to the voltage at the terminals of the source 24.

Figure 5:
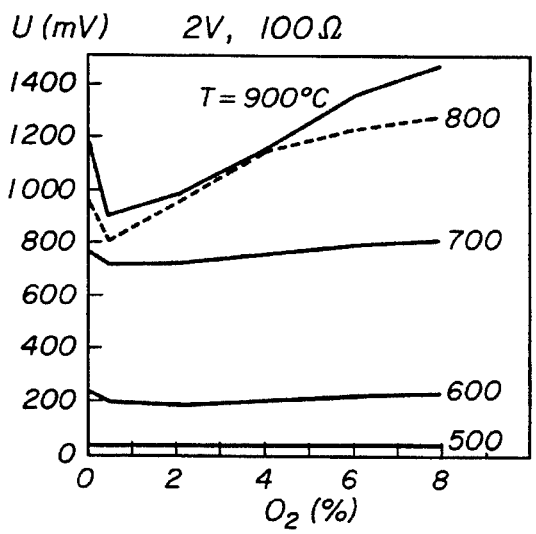

This was, however, no longer the case when a value of the resistor 25 equal to 100 Ohm was chosen. FIG. 5, illustrating such a case, shows that, for a voltage of 2 volt at the terminals of the source 24 the intensity of the current flowing into the electrodes is no longer a linear function of the oxygen content of the gaseous medium, when measurements are made at above 700° C.

Figure 6:
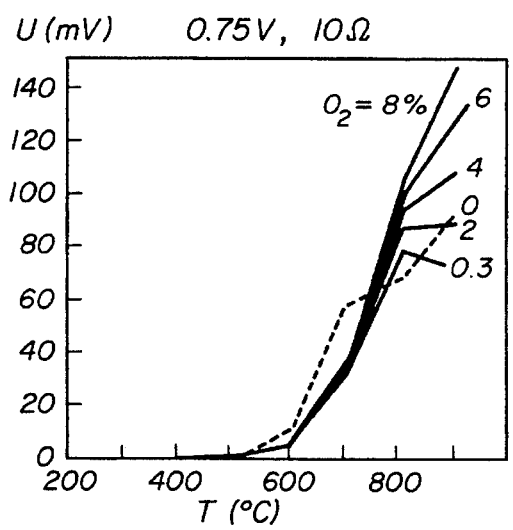
Figure 7:
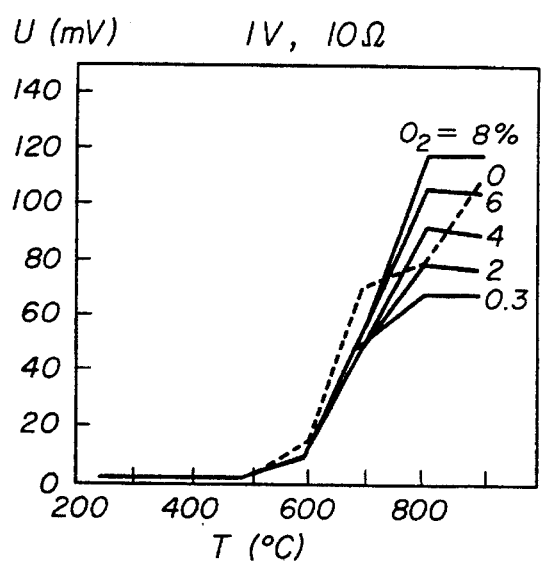
Figure 8:
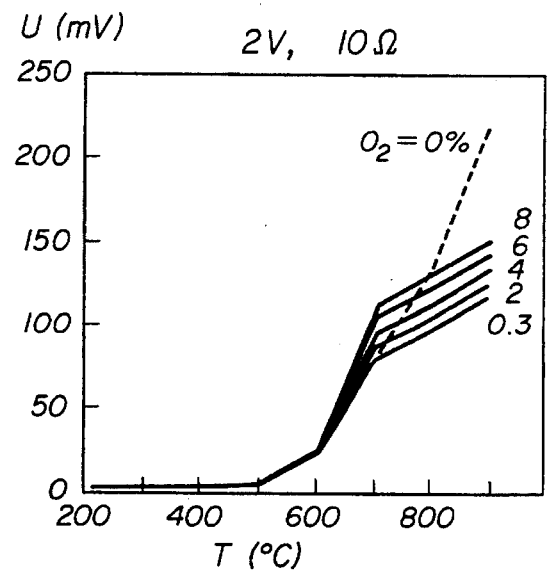
Figure 9:
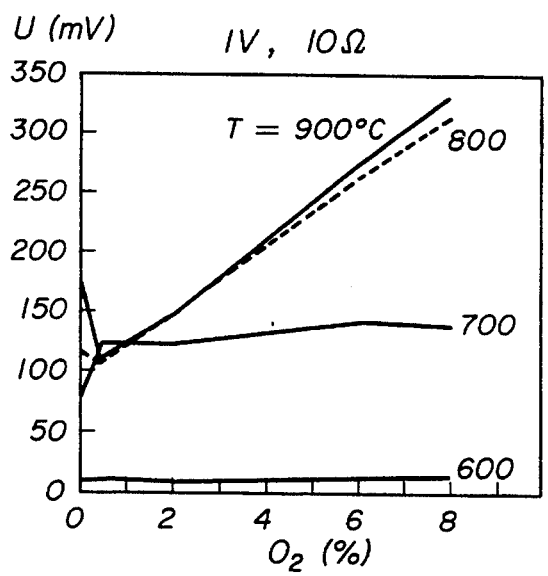
Figure 10:
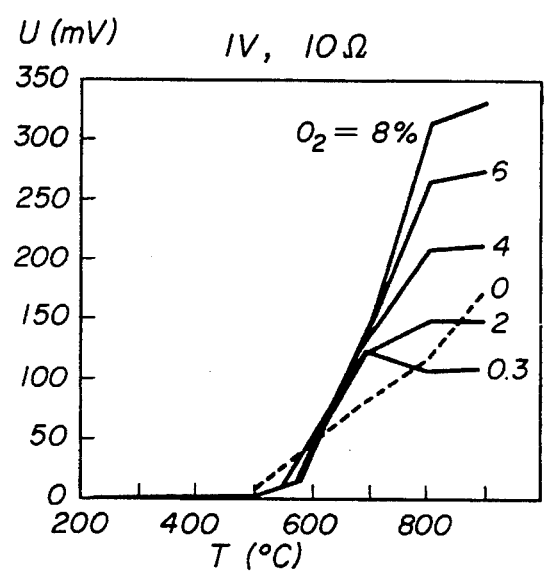

It is noted, in studying FIGS. 6 to 8 representing the variation of the current in the electrodes for oxygen contents between 0 and 8% and for supply voltages between 0.75 and 2 volt, that the response of the sensor as a function of the temperature is dependent on the value of the voltage at the terminals of the source 24 when measurements are made at above 700° C. For a voltage of 1 volt this response is independent of the measuring temperature as from approximately 800° C. When the value of the resistor of 25 was 10 Ohm, the sensitivity of the installation was approximately 0.9 mA/%$O_2$. This sensitivity was less when using a resistor 25 with a value of 100 Ohm (FIG. 5).

Example 2

A second series of tests, carried out using a tube similar to the above tube, covered on its inner face with a porous electrode, according to example 1, shows the behaviour of another embodiment of the sensor according to the invention.

A 0.9 μm thick platinum layer was deposited on the entire outer face of the tube by means of cathode sputtering, by the same method as above but leaving uncoated areas of about 100 μm size, in order to form an electrode comprising areas in which the molecular oxygen can come into contact with the electrolyte. It was shown that the sensor formed in this way and mounted in an installation according to FIG. 2 with a resistor 25 of 10 Ohm and using air as the reference gas provided a linear function of the oxygen content of a gaseous mixture in contact with the platinum electrode; this being for an oxygen content at least equal to 0.4% at a temperature greater than 500° C., when the supply voltage at the terminals of the source 24 was between 0.75 and 2 volt. It is further noted that the behaviour of this sensor, as a function of the temperature, was dependent on the different values of the supply voltage. The response of the sensor was even virtually independent of the temperature when this supply voltage was between 0.75 and 1 volt and when the measuring temperature was greater than approximately 800° C. The gaseous mixture used had an oxygen content between 0 and 8%.

Example 3

The sensor used for this third example was formed by a zirconia tube covered on its inner face by a porous platinum electrode as in example 1, and on its outer face by a layer made of a metal oxide mixture (15.57% by weight of NiO, 16.48% by weight of $Mn_2O_3$ and 67.98% by weight of $La_2O_3$). This mixture was in the form of a homogeneous powder, the grains of which were between 45 and 75 um in size.

Figure 11:
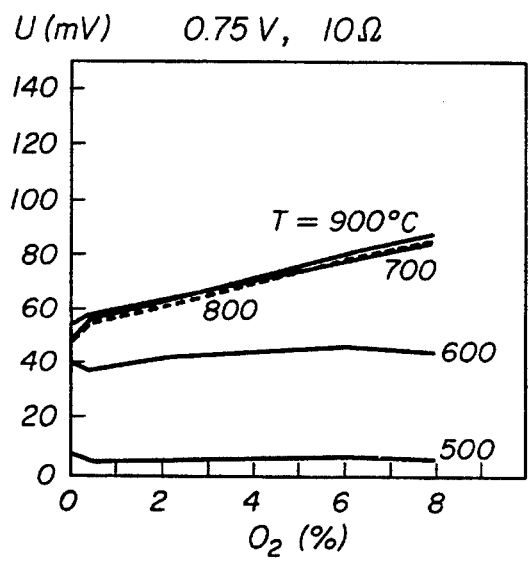
Figure 12:
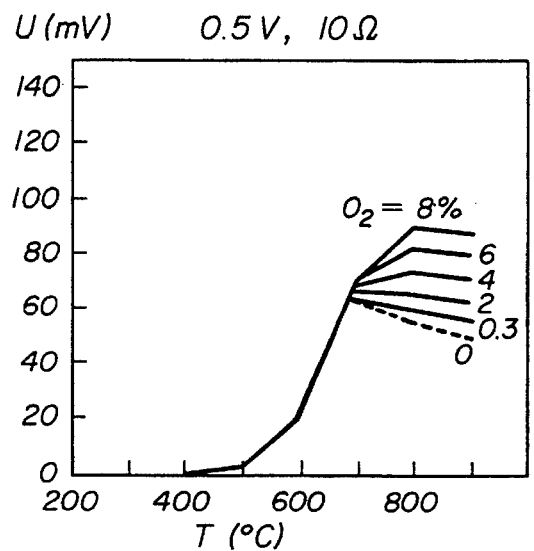
Figure 13:
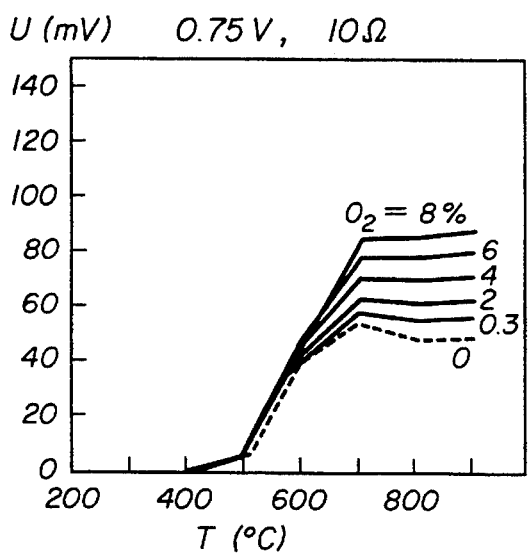
Figure 14:
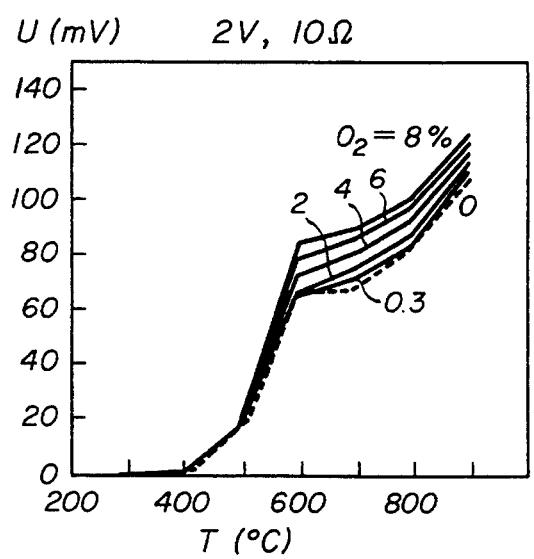

In order to make this metal oxide electrode, a deposit was produced by plasma spraying with a jet of gas composed of 10% hydrogen and 90% nitrogen, with a flow of 3.6 m³/h, heated electrically with 32 kW powder. Thus 10 g of powder was sprayed onto the tube rotating about its longitudinal axis at 3 revs/seconds, the powder being introduced into the jet at a rate of 1 g/second. A subsequent heat treatment (1 hour at 1000° C., heating and cooling down at a rate of 900° C./hour) for thermally stabilising the electrode, resulted in a layer sufficiently thick to be impervious to molecular oxygen being obtained. A plurality of holes (diameter 1 mm) according to FIG. 2b were made by boring through this oxide layer. The oxygen was allowed to come into contact with the zirconia forming the tube, by way of these holes. As in the preceeding examples, it was possible to make use of this sensor in such a way that it behaved as a linear function of the oxygen content of a gaseous mixture brought into the presence of the metal oxide electrode, at operating temperatures greater than 500° C. for oxygen contents greater than 0.5% and for a supply voltage between 0.5 and 2 volt. FIG. 11 (voltage equal to 0.75 volt) shows such behaviour for oxygen contents less than 8% at different temperatures. Starting from approximately 600° C., the value of the supply voltage influenced the behaviour of this sensor as a function of the temperature. For a voltage of 0.75 to 1 volt and starting from approximately 700° C., the response of the sensor was even virtually independent of the temperature (FIG. 12). FIGS. 12, 13 and 14 illustrate the development of the response of this last sensor as a function of the temperature, for supply voltages of 0.5, 0.75 and 2 volt respectively.

Comparison of the FIGS. relating to the sensor with electrodes according to the invention made of platinum with the FIGS. relating to the sensor with metal oxide electrodes shows that for oxygen contents greater than approximately 0.6%, the response of the different sensors is not dependent on the nature of the electrodes.

This observation does not apply when measuring oxygen contents less than 0.6% since the catalytic effect of the platinum electrodes in particular with respect to carbon dioxide altering the oxygen concentration close to the solid electrolyte, has a considerable influence on the value of the electric signal generated by the sensor.

We claim:

1. An electrolytic cell sensor for determining the oxygen content of a sample gas, the sensor comprising:

(a) first electrode means acting as an anode, for the conversion of $O^-$ ions to $O_2$ gas, which anode is not conductive of ions;

(b) second electrode means, acting as a cathode, for the conversion of $O_2$ to $O^-$ ions, said cathode being formed from a nonporous electroconductive material which is not conductive of ions;

(c) solid electrolyte means for conducting $O^-$ ions between said anode and said cathode; the electrolyte means separating said electrodes and being impervious to the passage of $O_2$, the cathode being in electronic contact with the electrolyte means and exposed to a sample gas; the anode being in electronic contact with the electrolyte means and exposed to a reference gas;

(d) power means for applying a DC current across said electrode means;

wherein the nonporous cathode material is shaped so as to expose said electrolyte means directly to said sample gas, an area of sample gas/electrolyte contact being defined by a cathode/electrolyte junction boundary line;

wherein the ionic resistance of said electrolyte means is less than $10^4$ ohm/cm of said cathode/electrolyte junction boundary line;

wherein the voltage applied by said power means is from 0.2 to 20 volts/cm of said cathode/electrolyte junction boundary line;

and wherein the electrolyte is heated to a temperature of at least 500° C., so that the current flowing across the electrodes of the sensor is controlled by the rate of ionization of $O_2$ in the sample gas at said area of sample gas/electrolyte contact.

2. A device according to claim 1, wherein the material forming the anode is pervious to oxygen gas.

3. A device according to claim 1, wherein the cathode and anode are both formed from material impervious to oxygen gas.

4. A device according to claim 1 wherein the electrolyte body has the form of a tube open at one of its ends.

5. A device according to claim 4 wherein the cathode covers a cylindrical portion of the tube starting from the open end of said tube and extending away from said end.

6. The device according to claim 4, characterized in that the sensor, closed at one of its ends, is between 10 and 1000 µm thick, the cathode is in the form of a cylinder extending over a portion of the height of the tube starting from the open end of the tube, and defines a junction boundary the total perimeter of which is of the order of 1 cm in length, the anode covering the inner face of the tube being pervious to oxygen.

7. The device according to claim 6, characterized in that the means for applying voltage is such that the electric signal representative of the oxygen content of the exhaust gas depends by not more than about 10% on the temperature of the said exhaust gas for measurements taken at more than 700° C. approximately.

8. A device according to claim 1, wherein there are interruptions in the cathode in the form of a plurality of holes distributed over at least one portion of its surface.

9. The sensor of claim 1 wherein said junction boundary is defined by holes in said impervious cathode material, said holes being 100 µm or more in diameter.

* * * * *